United States Patent [19]

Morrison

[11] Patent Number: 4,609,370

[45] Date of Patent: Sep. 2, 1986

[54] SURGICAL NEEDLE ASSEMBLY AND APPARATUS FOR ATTACHMENT ON A SURGICAL NEEDLE ASSEMBLY

[76] Inventor: Peter C. Morrison, 2919 Hillsdale Dr., Visalia, Calif. 93291

[21] Appl. No.: 645,697

[22] Filed: Aug. 30, 1984

Related U.S. Application Data

[63] Continuation-in-part of Ser. No. 505,949, Jun. 20, 1983, abandoned.

[51] Int. Cl.⁴ .............................................. A61M 5/00
[52] U.S. Cl. .................................... 604/165; 604/274; 128/754
[58] Field of Search ................................ 604/158–170, 604/272–274; 128/753, 754; 215/305

[56] References Cited

U.S. PATENT DOCUMENTS

| | | | |
|---|---|---|---|
| 1,583,019 | 5/1926 | Simmons | 215/305 X |
| 1,601,709 | 10/1926 | Anderson | 604/164 |
| 1,863,081 | 6/1932 | Bellows | 215/305 |
| 2,623,520 | 12/1952 | Bamford et al. | 604/165 |
| 3,348,544 | 10/1967 | Braun | 604/164 |
| 3,540,447 | 11/1970 | Howe | 604/165 |
| 3,585,986 | 6/1971 | Krug | 604/165 |
| 4,192,305 | 3/1980 | Seberg | 604/165 |
| 4,233,974 | 11/1980 | Desecki et al. | 604/165 |
| 4,345,606 | 8/1982 | Littleford | 604/165 |
| 4,362,156 | 12/1982 | Feller et al. | 604/165 |

Primary Examiner—Dalton L. Truluck
Attorney, Agent, or Firm—Worrel & Worrel

[57] ABSTRACT

A needle assembly for hand-held use in performing medical procedures having a first needle having a hollow shaft, the shaft having a pointed tip having a surface disposed at a predetermined angular relation to the longitudinal axis of the shaft; a second needle dimensioned for close-fitting removable insertion within the shaft; locking means for retaining the first and second needle in a fixed attitude relative to each other; and guide means adapted to indicate the attitude of deployment of the tip during use of the needle assembly in medical procedures. Also, an apparatus adapted for attachment on a conventional needle assembly for indicating the disposition of the tip thereof and for manipulating the needle assembly in an operative environment.

5 Claims, 13 Drawing Figures

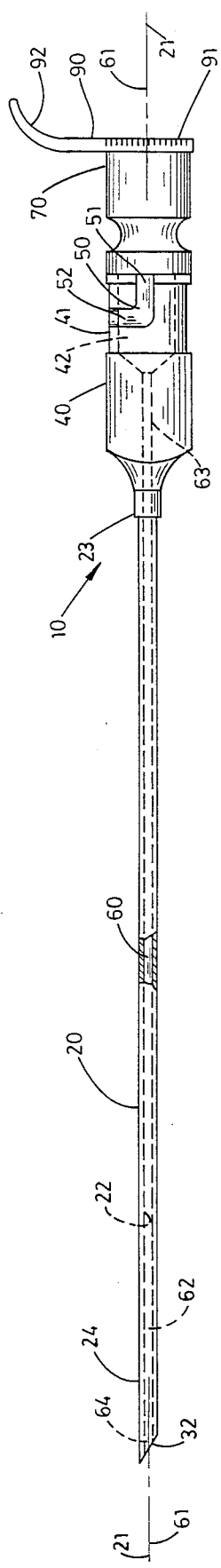
FIG. 2
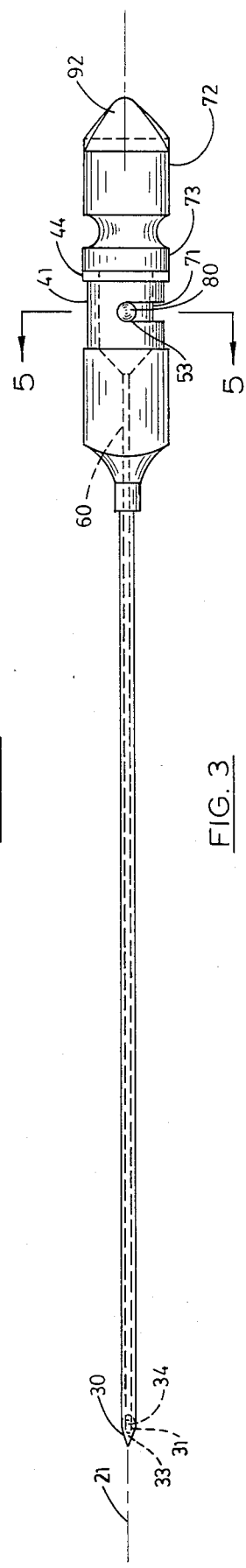
FIG. 3
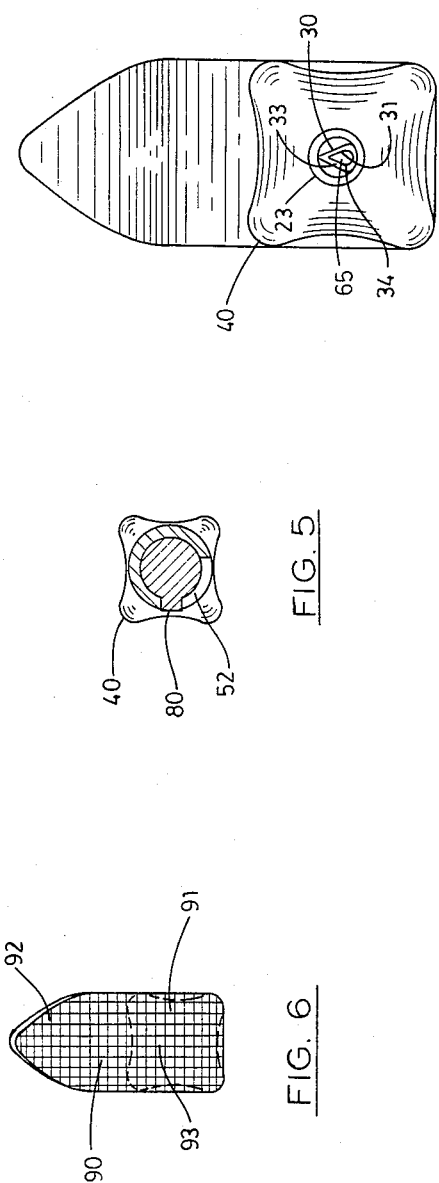
FIG. 4
FIG. 5
FIG. 6

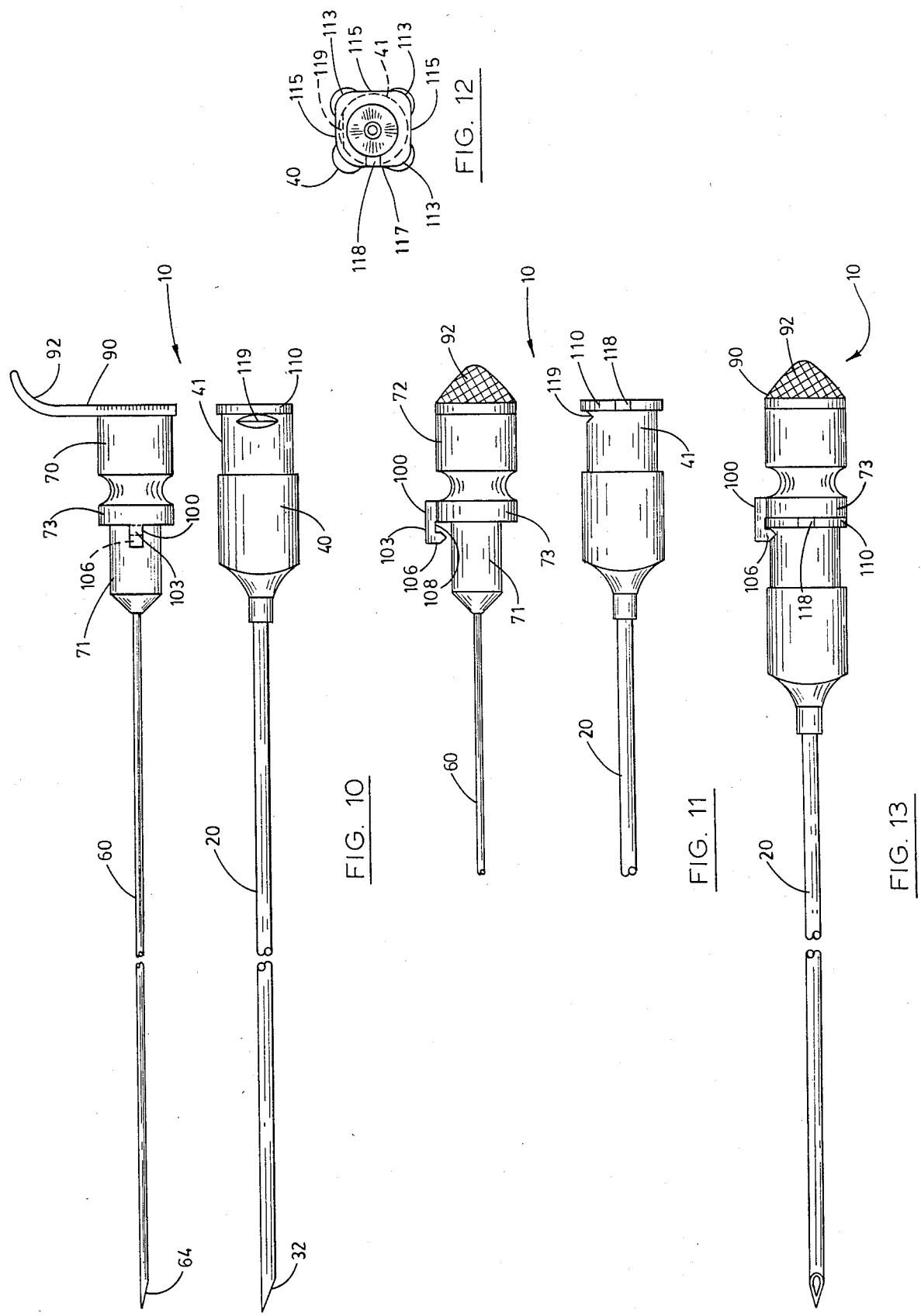

SURGICAL NEEDLE ASSEMBLY AND APPARATUS FOR ATTACHMENT ON A SURGICAL NEEDLE ASSEMBLY

BACKGROUND OF THE INVENTION

This is a continuation-in-part application of application Ser. No. 505,949, filed June 20, 1983, now abandoned.

FIELD OF THE INVENTION

The present invention relates to a needle assembly for use in medical procedures and the like and more particularly to such an assembly adapted for intervening within human intervertebral disc tissue for the introduction of diagnostic and therapeutic fluids therein.

DESCRIPTION OF THE PRIOR ART

The medical profession has long sought effective methods in the diagnosis and treatment of herniated vertebral discs, and particularly such herniations located in the lumbar region of the spine. The therapeutic course chosen for a given patient may be conservative, aggressive, or a combination of both. Among the more conservative forms of treatment are confining the patient to bed, restricting the patient's activities, and providing analgesic therapy for relief from pain. The more aggressive course of therapy often involves surgical intervention to remove the herniated disc in whole or in part.

Such methods, while indicated in a number of situations, suffer from a variety of drawbacks and inadequacies. Restriction of the patient to bed forces the patient to refrain from work, recreation, and other normal daily activities which may require ambulation. The inconveniences and hardships occasioned by such confinement of the patient are myriad. Analgesic therapy, although effective in some cases in alleviating lower back and leg pain, is more often directed toward an amelioration of symptoms rather than a prevention of their cause. Surgical techniques, such as laminectomies and the like, are frequently resorted to only after more passive therapeutic methods have been exhausted, and the post-operative course of the patient is frequently attended by prolonged periods of discomfort, pain, and immobility required to permit healing. It is also well known that such surgery often necessitates the use of anesthesia, the risks of such use being preferably avoided.

Relatively recent in origin is a technique known as chemonucleolysis which was developed for use primarily in treating herniated discs. The technique is well known as being associated with few of the known drawbacks commonly associated with the traditional therapeutic methods. In essence, the chemonucleolysis technique involves the insertion of a needle into the tissue of the herniated portion of the intervertebral disc to permit the delivery of an enzyme, such as chymopapain or the like to the operative site to digest or shrink the extruded tissue. It is desirable that the enzyme be injected only into the extruded disc material and, therefore, precise deployment of the needle tip is necessary to insure accurate and controlled delivery of the fluid enzyme carrier.

In diagnosed situations in which chemonucleolysis is indicated, the need for surgery and a protracted post-operative convalescent course are often obviated. Patients treated using this technique frequently are permitted to become ambulatory on the same day on which the treatment occurs, and post-treatment back and leg pain is usually minimized. Further, the patient can more readily resume normal daily activities, including the performance of work.

The surgical needle assemblies known in the prior art and employed in performing the technique of chemonucleolysis are commonly comprised of two needles: a first, outer needle or cannula; and a second, inner needle or stylet. The cannula has an elongated, tubular shaft having an interior bore of predetermined diameter throughout its length. At one end, the cannula has a beveled tip providing an apertured surface disposed in predetermined angular relation to the longitudinal axis of the shaft. Fluid transmitted through the bore is known to tend to follow a flow path relative to the longitudinal axis substantially corresponding to the angular disposition of the apertured surface upon exit therefrom. At the opposite end, the cannula has a hub portion providing a cavity of greater diameter than that of the bore. The stylet has an elongated shaft dimensioned for slidable insertion within the bore of the cannula and mounts a neck portion adapted to be received within the cavity of the cannula hub portion when the stylet shaft is inserted within the cannula bore. Remote from the stylet hub portion is its tip, the tip commonly being beveled similarly to the beveled tip of the cannula, whereby the respective beveled tips provide facing surfaces which lie in a substantially common plane when the shaft of the stylet is fully inserted within the bore of the cannula. An embossed portion of the stylet hub portion is sometimes provided to engage a similarly dimensioned notch or groove in the hub portion of the cannula, thus providing a means for insuring insertion of the stylet within the cannula in a predetermined attitude relative to it. In some needle assemblies, the cannula or stylet may be grooved, embossed, or otherwise marked with a form of indicium intended to remain in fixed, known relation to the angular disposition of the beveled tips, such indicia being adapted to remain outside of the bodily tissues during the performance of the technique, whereby reference may be had thereto in order to ascertain the direction in which the facing surfaces of the tips are disposed when such is not visible.

The needles heretofore known in the art suffer a number of drawbacks and deficiencies. For instance, in view of the aforementioned tendency of fluids to follow a substantially known flow path relative to the longitudinal axis of the needle shaft, in performing chemonucleolysis and related intervertebral disc therapy, it has been known that it would be desirable to be able precisely and accurately to deploy the beveled tip in a predetermined attitude within a predetermined region of the spinal disc tissue, whereby the fluid can accurately and controlledly be introduced primarily into the tissue to be treated. Moreover, in passing the tip of the needle through the bodily tissues surrounding the spinal disc, it is often necessary to maneuver the tip around and over various bony prominences of the vertebrae themselves as well as portions of the spinal nerves emitting from the spinal canal. It has been found that the beveled tip of the conventional needle assemblies acts much in a fashion of the curved tip portion of a snow ski or the like: that is, the tip has a tendency to ride away from material encountered by its surface. Such tendency may most advantageously be exploited by the user of the needle assembly only if means are provided for both instantaneously determining the disposition of the surface of the beveled tip and for transmitting directed force precisely to manipulate the beveled tip throughout a wide range of attitudes. However, such means have heretofore not been known in the prior art and, therefore, the full benefits of intradiscal therapeutic techniques such as chemonucleolysis have been difficult, if not impossible, to obtain employing conventional needle assemblies.

Further, in many procedures employing a dual needle assembly, the assembly is first inserted as a unit, the inner needle being then grasped by its head or neck portion and withdrawn to permit the injection of fluids through the outer needle via a syringe or the like. Inasmuch as chemonucleolysis and like procedures are commonly performed employing sterile technique, grasping the head portion may present a potential contamination risk.

Subsequent to such injection, the inner needle is reinserted, and the assembly is left in place for a predetermined period of time. However, it has been found that the fluid so injected often creates back pressure on the assembly, resulting in displacement of the inner needle and consequent leakage of fluid from the treated area. Insofar as applicant is aware, no needle assembly known in the art provides means for preventing such displacement.

Therefore, it has long been known that it would be desirable to have a needle assembly adapted to permit the precise and accurate delivery of fluids into predetermined bodily tissue areas and which provides the user thereof with means for continuously and simultaneously determining the disposition of the tip of the assembly within the bodily tissue and for precisely manipulating the tip for the directed movement thereof through such tissue. Further, it has long been known that it would be desirable to have a needle assembly which can securely and selectively be deployed in a locked attitude to prevent accidental or casual disengagement of the assembly components.

OBJECTS AND SUMMARY OF THE INVENTION

Therefore, it is an object of the present invention to provide an improved surgical needle assembly having a longitudinal axis and a tip disposed in predetermined angular relation thereto for hand-held and manipulated insertion within bodily tissues and which is capable of being so manipulated and inserted with a precision heretofore unobtainable.

Another object is to provide such an assembly which provides means capable for permitting continuous and reliable ascertainment by a user thereof of the attitude of deployment of the tip when such is inserted within bodily tissues and is not visible.

Another object is to provide such an assembly having means for retaining the component needles thereof against accidental disengagement thereof when deployed in an operative attitude. Another object is to provide such an assembly which can be employed with minimal risk of contamination during use thereof in medical procedures.

Another object is to provide such an assembly which is adapted for use in medical procedures requiring the delivery of fluids into bodily tissues and which is adapted to minimize the possibility of accidental leakage of such fluids from such bodily tissues when the assembly is inserted within the tissues.

Another object is to provide such an assembly of such durable construction as virtually to preclude damage thereto or deterioration thereof during its lifetime.

Another object is to provide such an assembly which enables the full exploitation of therapeutic procedures such as chemonucleolysis which require extremely accurate, directionally controlled transmission of fluids into bodily tissues.

Another object is to provide such an assembly which is characterized by ease of deployment, simplicity of construction, and which can be sold at a nominal price.

Another object is to provide such an assembly which is compact and capable of being effectively held and manipulated in one hand by the user thereof.

Another object is to provide an apparatus which can be deployed upon a conventional needle assembly to provide such assembly with many of the manipulative advantages obtained by the preferred embodiment.

Another object is to provide such an apparatus which can be deployed in a known relation to the longitudinal axis of a conventional needle assembly having an angularly disposed tip whereby the attitude of deployment of such a tip within bodily tissues can be ascertained by reference to such guide member.

Another object is to provide such an apparatus which can be constructed so inexpensively as to be disposable after single uses thereof.

Further objects and advantages are to provide improved elements and arrangements thereof in an assembly and guide member for the purposes described which are dependable, economical, durable and fully effective in accomplishing their intended purposes.

BRIEF DESCRIPTION OF THE DRAWINGS

FIG. 2 is a side elevation of the needle assembly of FIG. 1 shown depolyed in a locked attitude.

FIG. 3 is a view of the needle assembly of FIG. 1 rotated 90° about its longitudinal axis from the attitude shown in FIG. 2.

FIG. 4 is an end view of the needle assembly deployed in a locked attitude.

FIG. 5 is a transverse section taken on line 5—5 in FIG. 3.

FIG. 6 is a view taken from the end opposite that shown in FIG. 4.

FIG. 10 is a fragmentary side elevation of the components of the needle assembly shown disengaged from each other and illustrating an alternative means for locking the components in an operative attitude.

FIG. 11 is a fragmentary bottom plan view of the components of the needle assembly of FIG. 10.

FIG. 12 is an end view of one of the components of the needle assembly of FIG. 10.

FIG. 13 is a view of the needle assembly of FIG. 10 shown in a locked attitude.

DESCRIPTION OF THE PREFERRED EMBODIMENT

Surgical Needle Assembly

Figure 1:
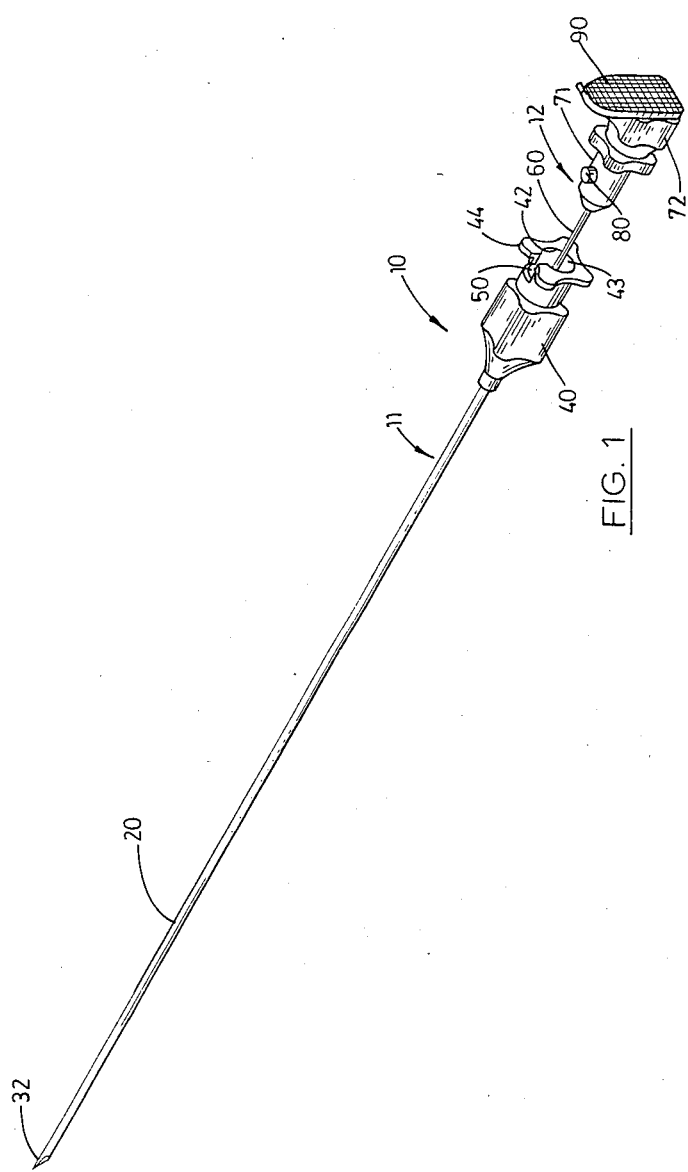
FIG. 1 is a perspective view of the needle assembly embodying the principles of the present invention shown in a partially disengaged attitude.

Referring more particularly to the drawings, the needle assembly embodying the principles of the present invention is shown in perspective in FIG. 1 and is designated generally by the numeral 10. As shown therein, the needle assembly generally provides a first needle, or cannula 11, and a second needle, or stylet 12.

As can best be seen in FIGS. 2 and 3, the cannula 11 has an elongated shaft 20 of predetermined length measured along a longitudinal axis 21. The shaft provides a passage or bore 22 of predetermined diameter extending axially therethrough from a hub end portion 23 to a delivery end portion 24, substantially coincident with the longitudinal axis.

As can best be seen by reference to FIGS. 2, 3 and 4, the delivery end portion 24 has an outer edge 30 and an inner edge 31 disposed in a substantially common plane and defining a pointed tip 32 having a surface 33 bounding an aperture 34. The surface 33 is disposed in predetermined angular relation to the longitudinal axis 21. Although the angle, or bevel, of the surface 33 may be varied, it is preferable that the surface be disposed at an angle ranging from about 22° to about 30° in relation to the longitudinal axis 21, for use of the assembly in performing techniques such as chemonucleolysis and the like.

The hub end portion 23 of the shaft 20 mounts a hub 40 dimensioned to be grasped in the fingers of a user thereof. The hub provides a substantially cylindrical wall 41 bounding a cavity 42 communicating between the bore 22 of the shaft 20 and an exterior opening 43 bounded by an endmost shoulder portion 44.

The hub 40 providing a locking channel 50 of substantially L-shaped configuration cut within the wall 41. The locking channel has a primary slot 51 disposed substantially parallel to the longitudinal axis 21 and extending from the shoulder portion 44 incompletely toward the hub end portion 23 of the shaft 20. Continuous with and substantially perpendicular to the primary slot is a secondary slot 52 disposed circumferentially approximately one-quarter of the distance around the wall 41 of the hub 40. the secondary slot has a terminus 53.

The stylet 12 provides an elongated, solid shaft 60 of predetermined length substantially symmetrical about a longitudinal axis 61. The shaft has a first end portion 62 and an opposite, second end portion 63. The first end portion 62 terminates in a tip 64 having a surface 65 disposed in predetermined angular relation to the longitudinal axis 61. In the preferred embodiment of the present invention, the angle defined by the surface of the tip 65 and the longitudinal axis 61 is substantially equal to that defined by the surface 33 of the tip 32 of the cannula shaft 20 and the longitudinal axis 21 of the cannula shaft. It is preferable that the shaft 60 be dimensioned for close-fitting, removable insertion within the bore 22 of the cannula, whereby the bore can be substantially occluded by the insertion of the stylet shaft therein.

The second end portion 63 of the stylet shaft 60 mounts a handle member 70. The handle member provides a neck portion 71 and a head portion 72. The neck portion is dimensioned for substantially close-fitting removable insertion within the cavity 42 of the hub 40. A shoulder-engaging portion 73 is provided intermediate the neck portion 71 and the head portion 72, whereby upon substantially complete insertion of the neck portion within the cavity 42, the shoulder-engaging portion 73 is disposed substantially in close-contact with the shoulder 44 of the hub 40, and the head portion 72 is disposed substantially external of the cavity 42.

A locking post or pin 80 is mounted on the neck portion 71 substantially perpendicularly to the longitudinal axis 61 of the shaft 60. The locking pin is dimensioned closely to be received within the locking channel 50 upon insertion of the neck portion 71 within the cavity 42 of the hub, and is adapted tensively to be retained in captured relation within the terminus 53 of the secondary slot 52 upon disposition therein.

Mounted on the head portion 72 is a substantially transversely projecting arm or guide member 90. In the preferred embodiment of the present invention, the guide member has a substantially flat portion 91, disposed substantially perpendicularly to the longitudinal axis of the stylet shaft 60, and a substantially curved portion 92, both portions providing a scored surface 93. The curved portion extends substantially outwardly, curving rearwardly away from the head portion 72. As can best be seen by reference to FIGS. 3 and 4, the guide member 90 is deployed in a fixed, predetermined relation to the locking pin 80 and the surface 65 of the tip 64 of the shaft 60. In the preferred embodiment, the guide member 90 is aligned with the locking pin 80 and projects remotely from the surface 65 of the tip 64 relative to the longitudinal axis 61. Thus, the disposition of the surface of the tip relative to the longitudinal axis can be determined continuously by reference to the disposition of the guide member 90.

Alternative means for lockably engaging the cannula 11 and stylet 12 in an operative attitude are illustrated in FIGS. 10, 11, 12 and 13. As shown therein, the locking pin 80 is removed from the neck portion 71 of the stylet 12. The shoulder-engaging portion 73 mounts a locking member 100 having a tongue portion 103 of predetermined length extending substantially parallel to the longitudinal axis 61 and spaced from the neck portion 71. The tongue portion 103 provides a depending tab 106 disposed normally to the longitudinal axis and, together with the tongue portion and the shoulder-engaging portion 73, the tab defines a notch 108 of predetermined dimensions. Preferably, the tongue portion 103 is disposed approximately 90° about the longitudinal axis from the curved portion 92 of the guide member 90. It is desirable that the locking member be constructed of resilient metal, plastic or other suitable material.

The shoulder portion 44 of the hub 40 of the cannula 11 is replaced by a substantially rectangular flange 110 having substantially rounded corners 113 and four edges 115. Three of the edges are dimensioned to extend from the wall 41 in the manner of a lip. A fourth edge 117 is substantially linear and has a portion substantially tangential with the curvature of the wall 41. The fourth edge 117 provides an indicator slot 118 for alignment of the locking member 100 in the operation of the needle assembly 10, as is described in greater detail below.

The wall 41 is scored to define a substantially flat groove 119 of predetermined dimensions disposed substantially perpendicularly to the longitudinal axis 21 and further disposed substantially perpendicularly to the fourth edge 117. Preferably, the flange 110 has a thickness in a longitudinal dimension adapted to permit the substantially close-fitting capturing thereof within the notch 108 of the locking member 100. Further, the groove 119 of the wall 41 is dimensioned for disposition of a portion of the tab 106 of the locking member 100 therein when the needle assembly 10 is disposed in an operative attitude.

Figure 9:
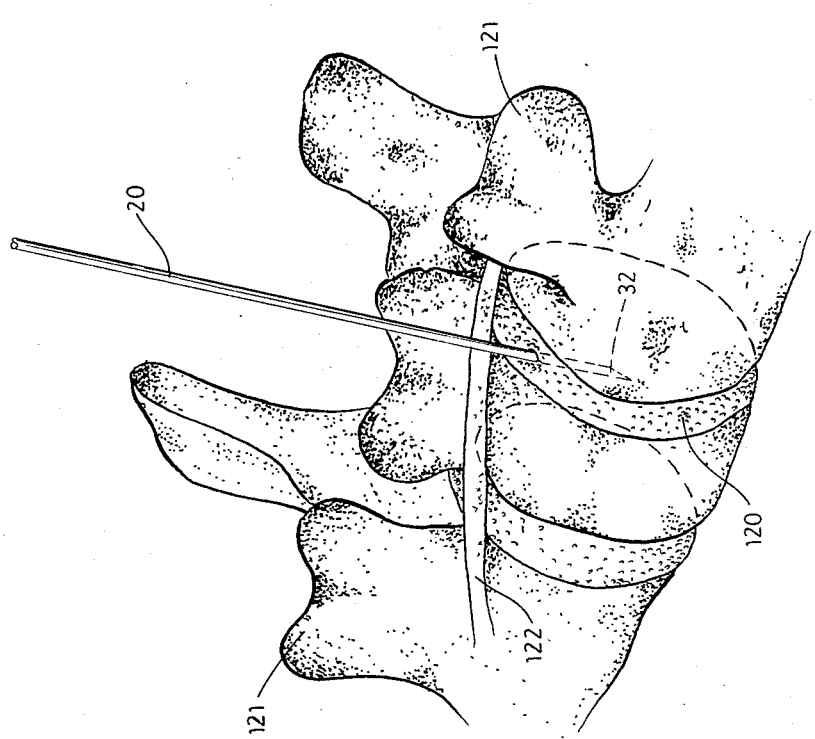
FIG. 9 is a view of a portion of the needle assembly of FIG. 1 shown deployed in a typical operative environment partially inserted in an intervertebral disc.

As is described in greater detail hereafter, the needle assembly 10 finds greatest utility in permitting accurate deploymen of the tip 32 within soft tissue, such as intervertebral discs 120 while avoiding environmental anatomical sturctures, such as bony prominences 121, spinal nerves 122 and the like, such as are illustrated in FIG. 9.

APPARATUS FOR ATTACHMENT ON A NEEDLE ASSEMBLY

Figure 8:
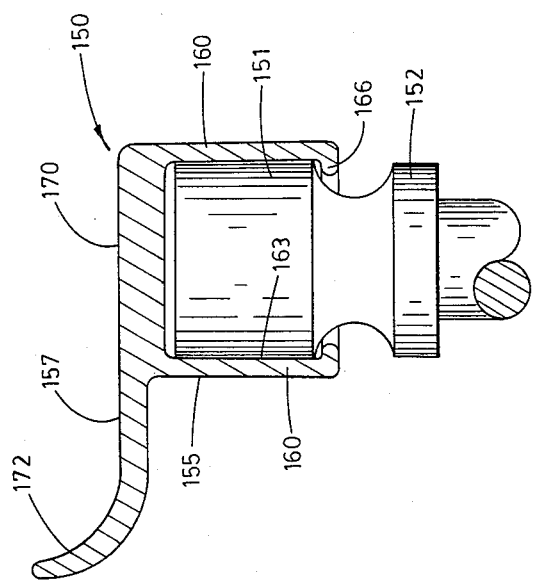
FIG. 8 is a transverse section taken on line 8—8 in FIG. 7.
Figure 7:
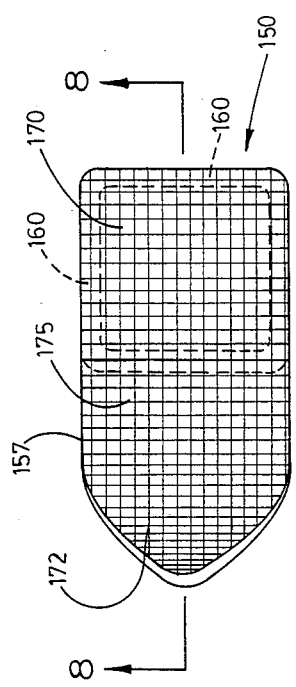
FIG. 7 is a top view of the apparatus of the present invention.

The apparatus of the present invention is designated generally by the numeral 150 in FIGS. 7 and 8. As shown therein, the apparatus, or cap member 150, is adapted to be deployed on the head portion 151 of a conventional surgical needle 152, shown fragmentarily in FIG. 8. It is preferable, although not necessary, that the cap member be constructed of a suitable synthetic material having moderate resiliency, thus enabling low production costs and permitting the cap member to be disposable after use. The cap member provides a body portion 155 and a guide portion 157. The body portion has walls 160 which can be configured as needed substantially closely to conform to the configuration of the head portion 151 of a particular surgical needle for which the cap member is designed. The walls 160 define a cavity 163 bounded by a lip 166 dimensioned to permit the cap member 150 to be removably snap-fitted upon the head portion 151 in capturing relation thereto.

The guide portion 157 of the cap member 150 is constructed substantially similarly to the guide member 90 of the needle assembly 10 of the preferred embodiment. The guide portion provides a substantially flat section 170 unitary with and surmounting the walls 160 and a curved extending section 172 projecting outwardly and away from the body portion 155. Thus, the cap member 150 can be deployed upon the head portion 151 of a conventional surgical needle to dispose the extending section 172 in a predetermined relation to the longitudinal axis thereof, and can enable the user of a conventional surgical needle to manipulate it substantially in the fashion of the improved needle assembly 10 of the present invention, as is described in greater detail below. The extending section 172 provides a surface 175 which is scored to afford an enhanced degree of friction upon engagement of a user's finger thereby.

OPERATION

The operation of the described embodiment of the present invention is believed readily apparent and is briefly summarized at this point.

In assembling the needle assembly 10 prior to use in a medical procedure such as the chemonucleolysis technique referred to previously, the cannula 11 can be grasped manually by the user thereof while the stylet 12 is also manually grasped. The tip 64 of the stylet is introduced through the exterior opening 43 of the hub 40 of the cannula and is then passed through the hub cavity 42 and inserted into the bore 22 of the cannula. The shaft 60 of the stylet is then passed through the bore 22. As the neck portion 71 is brought into proximity with the exterior opening 43, the locking pin 80 is aligned with the primary slot 51 of the locking channel 50. As the shaft is continued to be passed through the bore 22, the locking pin 80 is passed along the locking channel primary slot 51 until the neck portion 71 is fully inserted within the cavity 42 of the hub and engages same. The stylet 12 is then manually rotated about its longitudinal axis 61 to carry the locking pin 80 along the secondary slot 52 into engagement with the terminus 53 of the locking channel. The needle assembly 10 is thereby deployed in a locked attitude wherein the shafts 20 and 60 of the cannula 11 and the stylet 12, respectively, are disposed substantially coaxially. Further, in the locked attitude, the curved portion 92 of the guide member 90 is disposed in a predetermined relationship to the disposition of the surface 33 of the tip 32 of the cannula. The surface 33 and the curved portion 92 are thereby disposed substantially diametrically oppositely of each other about the longitudinal axes.

In the locked attitude, the needle assembly 10 can be manipulated as a unit, whereby manipulative force applied to the guide member 90, the hub 40, or the head portion 72 of the stylet will cause simultaneous resulting movement of both the stylet and the cannula.

The assembly 10 can be selectively disengaged by grasping the curved portion 92 of the guide member 90 and applying rotational force to the stylet about its longitudinal axis, whereby the locking pin 80 is moved along the locking channel 50.

In performing medical procedures involving the delivery of fluids into bodily tissues, the needle assembly 10 is first deployed in the locked attitude prior to insertion of the tip 32 into the tissues.

For purposes of manipulating the needle assembly as it is directed through the bodily tissues, the guide member 90 may be most advantageously employed by the user of the needle assembly by placing the index finger of the hand used to grasp the assembly against the surface 93 of the guide member, thereby permitting the index finger simultaneously to assist in the manipulation and application of force to the needle assembly and to act as a tactile means of sensing the direction of deployment of the surface 33 of the tip 32. As has been discussed above, the angular nature of the surface 33 causes the tip to plane away from tissue encountered thereby. As shown in FIG. 9, the tip 32 can thus be deployed within an intervertebral disc 120 after having been passed through bodily tissues and circumventing bony prominences 121 and spinal nerves 122. Thus, it can be readily appreciated that visualization of the progress of the tip of the assembly through the bodily tissues by use of fluroscopic or other radiologic imaging devices can be coordinated with great facility with the tactily indicated orientation of the needle assembly guide member 90. Further, it may be readily seen that minute changes in the course of the tip through the bodily tissues can be effected easily and continuously without interruptions for visual checks of the indicator means on the needle assembly. Thus, not only is the maneuverability of the needle assembly increased, but the precision of deployment of the tip is enhanced for the user thereof as well.

Further, the novel means provided for maintaining the needle assembly in a locked attitude insures that back pressure from fluid injected into the bodily tissues will not cause the stylet to be forced from the bore of the cannula with possible resulting leakage and loss of therapeutic fluids.

Deployment of the needle assembly 10 incorporating the alternative locking means illustrated in FIGS. 10, 11, 12 and 13, is substantially similar to that of the needle assembly described immediately above. That is, preliminarily, the tip 64 of the stylet is introduced through the exterior opening 43 of the hub 40 of the cannula and is then passed through the hub cavity 42 and inserted into and through the bore 22 of the cannula. As the neck portion 71 is brought into proximity with the exterior opening 43, the locking member 100 and, more particularly, the tab 106 thereof, are aligned with the indicator slot 118 of the flange 110. The stylet is passed axially until the neck portion 71 is fully inserted within the cavity 42 of the hub. The stylet is then rotated about its longitudinal axis 61 in the direction of the portion of the wall 41 bearing the groove 119. The tongue portion 103 of the locking member 100 is thus caused to ride up and over the rounded corner 113 disposed between the fourth edge 117 and the edge 115 corresponding to the portion of the wall 41 bearing the groove 119. Upon overcoming the corner, the tongue portion 103 and tab 106 of the locking member 100 resiliently rebound to dispose the edge 115 within the notch 108 and with the tab tightly inserted within the groove 119. Thus, the entire needle assembly 10 can be manipulated about the longitudinal axis as a unit without disengagement of the stylet and cannula either rearwardly due to back pressure or the like, or due to rotary forces directed tangentially to the longitudinal axis. The needle assembly can then be utilized in the manner described above.

The operation of the apparatus 150 of the present invention is also believed apparent. To utilize the apparatus, the body portion 155 is snap-fittingly deployed on the head portion 151 of a conventional needle assembly 152 with the head portion captured within the cavity 163. The curved, extending portion 172 is utilized to greatest advantage by deploying it in known relation about the longitudinal axis to the beveled tip of the needle assembly. Thereafter, the needle assembly is adapted to be employed substantially in the manner described above, although it is recognized that the advantages obtained by the locking means of the needle assembly 10 of the present invention may be lacking.

Thus, the apparatus of the present invention described herein provides a means by which conventional needle assemblies can be adapted to obtain many of the manipulative advantages afforded by the preferred embodiment.

Of course, although the needle assembly of the present invention is described in reference to its applicability to techniques such as chemonucleolysis, it is believed that the needle assembly will provide great advantage in a wide variety of medical procedures wherein the precise placement of needle tips and/or controlled delivery of fluids into bodily tissues is desirable. Therefore, the needle assembly of the present invention provides a markedly-improved device which can be accurately manipulated and maneuvered through bodily tissues to deliver fluids into such tissues with a precision and ease of manipulation heretofore not known in the art.

Although the invention has been herein shown and described in what are conceived to be the most practical and preferred embodiments, it is recognized that departures may be made therefrom within the scope of the invention, which is not to be limited to the illustrative details disclosed.

Having described my invention, what I claim as new and desire to secure by Letters Patent is:

1. A needle assembly comprising a first needle having an elongated hollow shaft having a longitudinal axis and providing a first end having a tip with a surface disposed in predetermined angular relation to the longitudinal axis, and an opposite, second end mounting a hub having a cavity therein; a second needle having an elongated shaft having a longitudinal axis and mounting a head portion of predetermined dimensions, the shaft being dimensioned for insertion within the first needle whereby, when so inserted, the longitudinal axis of the first needle and the second needle are disposed in substantially coaxial relationship and the needle assembly can be manipulated as a unit upon the application of mainpulative force thereto; a cap member dimensioned for removable mounting on said head portion in predetermined relation to the longiudinal axis of the second needle; and a guide mounted on the cap membe extending laterally therefrom in predetermined angular relation thereto for indicating the attitude of disposition of the tip of the first needle, whereby the guide is disposed in known relation to the longitudinal axis of the second needle when the cap member is deployed on the head portion thereof, said guide having a curved portion dimensioned to be engaged by a finger of a user thereof for application of manipulative force to the needle assembly.

2. A cap member removably coupled on the head portion of a needle assembly for hand-held, manual manipulation of the needle assembly in bodily tissue for the performance of a medical procedure, the cap member comprising a body portion having walls dimensioned substantially to conform to the head portion of the needle assembly to hold said body portion on the head portion of the needle assembly; and a guide portion having a substantially flat section mounted on the body portion and a curved section extending outwardly and away from the body portion, said guide portion being aligned with the needle assembly to permit determination of the position of the needle assembly continuously by reference to the disposition of the guide portion.

3. The cap member of claim 2 wherein the cap member is constructed of synthetic material having moderate resiliency.

4. The cap member of claim 2 wherein the guide portion is scored to afford an enhanced degree of friction upon engagement with the user's finger.

5. The cap member of claim 2 wherein the walls define a cavity bounded by lip, said cavity dimensioned to permit the cap member to be removably coupled upon the head portion of a needle assembly by the lip in capturing relation thereto.

* * * * *

UNITED STATES PATENT AND TRADEMARK OFFICE
CERTIFICATE OF CORRECTION

PATENT NO. : 4,609,370

DATED : September 2, 1986

INVENTOR(S) : Peter C. Morrison

It is certified that error appears in the above-identified patent and that said Letters Patent is hereby corrected as shown below:

Column 3, line 58, begin a new paragraph with the word "Another".

Column 4, line 42, delete "depolyed" and substitute ---deployed---

Column 5, line 45, delete "the" and substitute ---The---.

Signed and Sealed this

Sixteenth Day of December, 1986

Attest:

DONALD J. QUIGG

Attesting Officer      Commissioner of Patents and Trademarks